(12) United States Patent
Lorenzo-Zúñiga García et al.

(10) Patent No.: US 11,234,999 B2
(45) Date of Patent: *Feb. 1, 2022

(54) TOPICAL COMPOSITION FOR THE TREATMENT OF MUCOSAL LESIONS

(71) Applicants: FUNDACIÓ INSTITUT D'INVESTIGACIÓ EN CIÈNCIES DE LA SALUT GERMANS TRIAS I PUJOL, Badalona (ES); CENTRO DE INVESTIGACIÓN BIOMÉDICA EN RED, Madrid (ES)

(72) Inventors: Vicente Maria Lorenzo-Zúñiga García, Barcelona (ES); Ramon Bartolí Solé, Barcelona (ES); Jaume Boix Valverde, Barcelona (ES)

(73) Assignees: FUNDACIÓ INSTITUT D'INVESTIGACIÓ EN CIÈNCIES DE LA SALUT GERMANS TRIAS I PUJOL, Badalona (ES); CENTRO DE INVESTIGACIÓN BIOMÉDICA EN RED, Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/780,754

(22) Filed: Feb. 3, 2020

(65) Prior Publication Data

US 2020/0171073 A1  Jun. 4, 2020

Related U.S. Application Data (63) Continuation of application No. 15/553,968, filed as application No. PCT/EP2016/053928 on Feb. 25, 2016, now Pat. No. 10,561,680.

(30) Foreign Application Priority Data

Feb. 26, 2015 (EP) .................. 15382080

(51) Int. Cl.
| | |
|---|---|
| A61K 31/728 | (2006.01) |
| A61K 31/77 | (2006.01) |
| A61K 9/06 | (2006.01) |
| A61P 41/00 | (2006.01) |
| A61L 24/00 | (2006.01) |
| A61L 26/00 | (2006.01) |
| A61L 24/04 | (2006.01) |
| A61L 24/08 | (2006.01) |
| A61K 47/38 | (2006.01) |
| A61K 9/00 | (2006.01) |
| A61K 31/437 | (2006.01) |
| A61K 31/717 | (2006.01) |
| A61K 47/34 | (2017.01) |

(52) U.S. Cl.
CPC .......... *A61K 31/728* (2013.01); *A61K 9/0019* (2013.01); *A61K 9/06* (2013.01); *A61K 31/437* (2013.01); *A61K 31/717* (2013.01); *A61K 31/77* (2013.01); *A61K 47/34* (2013.01); *A61K 47/38* (2013.01); *A61L 24/0015* (2013.01); *A61L 24/0031* (2013.01); *A61L 24/043* (2013.01); *A61L 24/08* (2013.01); *A61L 26/008* (2013.01); *A61L 26/0023* (2013.01); *A61L 26/0052* (2013.01); *A61L 26/0066* (2013.01); *A61P 41/00* (2018.01); *A61L 2300/406* (2013.01); *A61L 2400/06* (2013.01)

(58) Field of Classification Search
CPC .............................. A61K 31/728; A61P 41/00
See application file for complete search history.

(56) References Cited

U.S. PATENT DOCUMENTS

| | | | |
|---|---|---|---|
| 5,843,470 A | 12/1998 | Reeve et al. | |
| 6,140,355 A | 10/2000 | Egidio et al. | |
| 10,561,680 B2 * | 2/2020 | Lorenzo-Z niga Garcia ............... | A61L 24/0015 |
| 2003/0225460 A1 | 12/2003 | Gostout et al. | |
| 2005/0266086 A1 | 12/2005 | Sawhney | |
| 2006/0280797 A1 | 12/2006 | Shoichet et al. | |
| 2008/0119437 A1 | 5/2008 | Lewis | |
| 2010/0291191 A1 | 11/2010 | Shoichet et al. | |

(Continued)

FOREIGN PATENT DOCUMENTS

| | | | | |
|---|---|---|---|---|
| CA | 2703807 A1 | 11/2011 | | |
| CN | 104027299 | * | 9/2014 | ............. A61K 31/77 |
| CN | 104645425 A | 5/2015 | | |

(Continued)

OTHER PUBLICATIONS

Charreau et al., "Poloxamer 407 as a Thermogelling and Adhesive Polymer for Rectal Administration of Short-Chain Fatty Acids" Drug Development and Industria Pharmacy vol. 27 No. 4 pp. 351-357 (Year: 2001).*

Stacey et al., "Radiation-induced small bowel disease: latest developments and clinical guidance" Therapeutic Advances and Chronic Disease vol. 5 No. 1 pp. 15-29 (Year: 2014).*

Luo et al., "Mucoadhesive and Elastic Films Based on Blends of Chitosan and Hydroxyethylcellulose" Macromolecular Bioscience vol. 8 pp. 184-192 (Year: 2008).*

English machine translation of CN 104027299, downloaded from https://worldwide.espacenet.com/ (Year: 2014).*

Mayol et al., "A novel poloxamers/hyaluronic acid in situ forming hydrogel for drug delivery: Rheological, mucoadhesive and in vitro release properties" European Journal of Pharmaceutics and Biopharmaceutics vol. 70 pp. 199-206 (Year: 1999).*

(Continued)

*Primary Examiner* — Eric Olson
(74) *Attorney, Agent, or Firm* — Squire Patton Boggs (US) LLP (57) ABSTRACT

It relates to a topical composition comprising specific amounts of: a) a hyaluronic acid or a pharmaceutically or veterinary acceptable salt thereof, b) one or more adhesive agents, and c) a non-absorbable antibiotic; to delivery devices comprising it; and to its uses in medicine, in particular, in the treatment and/or prevention of mucosal lesions; in the prevention of postpolypectomy syndrome; as adjuvant therapy to mechanical treatments in gastrointestinal perforations, and as sealant treatment in surgical anastomoses and leaks or fistulas in gastrointestinal tract.

14 Claims, 1 Drawing Sheet

(56) References Cited

U.S. PATENT DOCUMENTS

2014/0294770 A1 10/2014 Davis et al.
2016/0235715 A1 8/2016 Paris

FOREIGN PATENT DOCUMENTS

| CN | 105168238 A | | 12/2015 | |
|---|---|---|---|---|
| WO | WO 2000/19981 A1 | | 4/2000 | |
| WO | WO 2011/072399 A1 | | 6/2011 | |
| WO | WO 2013/006671 A2 | | 1/2013 | |
| WO | WO2014/063735 | * | 5/2014 | ........... A61K 31/728 |
| WO | WO 2016/135219 A1 | | 9/2016 | |

OTHER PUBLICATIONS

Bartolí, R., et al., "Colonoscopy in rats: An endoscopic, histological and tomographic study", World J. Gastrointestinal Endoscopy, May 16, 2013, 5(5):226-30.

Drug Bank entry on Bacitracin, downloaded from www.drugbank.ca, 2019: 9 pages.

Fuchs, et al: "Irinotecan in the treatment of colorectal cancer", Cancer Treatment Reviews, Elsevier, Nov. 1, 2006, vol. 32, No. 7, pp. 491-503, XP005674591.

Kibbe, et al: "Handbook of Pharmaceutical Excipients, Carbomer, Glycerin, Isopropyl Myristate, Isopropyl Glycol", Handbook of Pharmaceutical Excipients, American Pharmaceutical Assoc. Washington DC, Jan. 1, 2000, pp. 79-82; 220-222; 265-268; 336-339; 442-444, XP002511422.

Kunin, Calvin M. M.D., et al., "Absorption of orally administered Neomycin and Kanamycin—with special reference to patients with severe hepatic and renal disease", The New England Journal of Medicine, Feb. 25, 1960, 262: 380-385.

Lorenzo-Zúñiga, V., et al., "Microperforation of the colon: animal model in rats to reproduce mucosal thermal damage", J. Surgical Research, Jan. 29, 2014, 188(2):415-8.

Mayol, et al., European Journal of Pharmaceutics and Biopharmaceutics 2008; vol. 70, pp. 190-206.

Monkemuller, K., et al., "Advanced Colon Polypectomy", Clinical Gastroenterology and Hepatology, 2009, 7(6):641-652.

Niimi, Keiko, et al., "Subserosal injection of hyaluronic acid may prevent perforation after endoscopic resection", World J. Gastrointestinal Endoscopy, Oct. 15, 2009, 1(1):61-4.

Pelosini, Iva, et al., "Rifaximin a peculiar refamycin derivative: established and potential clinical use outside the gastrointestinal tract", Chemotherapy 2005, 1(1):122-130.

Seol, et al: "Biocompatibility and preclinical feasibility tests of a temperature-sensitive hydrogel for the purpose of surgical wound pain control and cartilage repair", Journal of Biomedical Materials Research, Jul. 1, 2013, pp. 1508-1515, XP55332285.

Somogyi, Andrew A., et al., "Evaluation of the intestinal absorption of Erythromycin in man: absolute bioavailability and comparison with enteric coated Erythromycin", Pharmaceutical Research 1995, 12(1): 149-154.

Wang, et al: "Development of rectal delivered thermos-reversible gelling film encapsulating a 5-fluorouracil hydroxypropyl-B-cyclodextrin complex", Carbohydrate Polymers, Applied Science Publishers Ltd., Oct. 19, 2015, vol. 137, No. 19, pp. 9-18, XP029344662.

Yamamoto, H., et al., "A novel method of endoscopic mucosal resection using sodium hyaluronate", Gastrointestinal Endoscopy 1999, 50(2): 251-256.

Chaibundit et al. Journal of Colloid and Interface Science 2010 351:190-196 (Year: 2010).

Dumortier et al. Drug Development and Industrial Pharmacy 2006 32:63-72 (Year: 2006).

Cho etr al. Drug Development and Industrial Pharmacy 1997 23(12):1227-1232 (Year: 1997).

Dewan et al. International Journal of Biological Macromolecules 2015 72:706-710 (Year: 2015).

U.S. Appl. No. 16/320,445 Pending claims, filed Nov. 13, 2020.

\* cited by examiner

TOPICAL COMPOSITION FOR THE TREATMENT OF MUCOSAL LESIONS

The present invention relates to a topical composition comprising hyaluronic acid, one or more adhesive agents, and a non-absorbable antibiotic, and to delivery devices comprising it. It also relates to its uses in medicine, especially as endoscopic shield to treat and/or prevent wounds caused or associated to therapeutic endoscopy.

BACKGROUND ART

Endoscopy is a minimally invasive procedure that allows diagnosing conditions inside the gastrointestinal, respiratory or urinary tract, by means of an endoscope which is inserted through a body passageway. Advances in endoscopic medicine have led to the development of therapeutic endoscopy that enables physicians to treat numerous conditions using endoscopic techniques such as the removal of polyps and early tumors.

Endoscopic polypectomy and hot biopsy have become routine electrosurgery procedures for the removal of colonic small or very small polyps in the course of colonoscopy. Other techniques such as endoscopic mucosal resections (EMR) and endoscopic submucosal resections (ESD) allow the removal of larger polyps or early-stage colorectal cancer, thus reducing the need for surgical intervention.

Although these techniques are generally very safe and convenient, in a few cases there are still post-operative complications such as bleeding, transmural thermal injury and perforation.

On the one hand, coagulation syndrome (also known as postpolypectomy electrocoagulation syndrome and transmural burn syndrome) may appear after polypectomy with electrocoagulation and refers to the development of abdominal pain, fever, leukocytosis, and peritoneal inflammation in the absence of frank perforation.

On the other hand, extensive bleeding may cause a surgical procedure to be terminated and might require a transfusion, whereas postoperative perforation is an especially serious adverse event, which generally requires emergency surgery.

Therefore, taking into account the large number of therapeutic endoscopy procedures carried out today, it is imperative trying to avoid such complications regardless of the limited (in percentage) number of cases with complications.

Several approaches for avoiding the post-operative complications after therapeutic endoscopy have been described, including, for example, clipping techniques after colorectal endoscopic resection. However, these procedures require special devices or are quite complex, and besides, the duration of clip persistence remains unknown. Furthermore, polyglycolic acid (PGA) sheets and fibrin glue have been described in the art as endoscopic tissue shields to cover wounds after colorectal endoscopic submucosal dissection (ESD).

According to this procedure, several PGA sheets need to be placed on the affected tissue with biopsy forceps. After the whole area is covered, it is sprayed with fibrin glue. However, this method requires a significant amount of time and is thought to be inefficient for covering large mucosal defects.

Niimi K. et al., World J. Gastrointest. Endosc. 2009, 1(1): 61-64, investigated the possible protective effect of a subserosal injection of hyaluronic acid (HA) after endoscopic resection (ER). However, according to the authors' conclusions, the study failed to show any preventative effects of HA on postoperative perforation.

Therefore, there is a need to develop a topical composition, which reduces or avoids post-operative complications after therapeutic endoscopy and contributes to the wound healing.

SUMMARY OF THE INVENTION

The inventors have developed a topical composition comprising specific amounts of a hyaluronic acid or a salt thereof, one or more adhesive agents, and a non-absorbable antibiotic which provides good healing properties and is suitable for the treatment of mucosal lesions and/or for the prevention of complications derived from mucosal lesions.

Additionally, the composition of the invention has the advantage that in applications such as after endoscopic therapy, it can easily and rapidly be applied without requiring any special or complex devices, and due to its viscosity and adhesion properties at body temperature, has the ability to remain adhered to the affected area for a long period of time, thus facilitating the physiological healing of the wound. As it is shown in the examples, the compositions of the invention reduce or even avoid the risk of perforation, show a higher mucosal healing rate, a higher physiological healing, and reduce inflammatory marker, such as TNF-α, in comparison to a composition consisting only of hyaluronic acid.

Therefore, a first aspect of the present invention relates to a topical composition comprising:
a) from 0.6 to 1.5 wt % of a hyaluronic acid or a pharmaceutically or veterinary acceptable salt thereof,
b) from 0.75 to 25 wt % of one or more adhesive agents, and
c) from 1.5 to 2.5 wt % of a non-absorbable antibiotic;
wherein all percentages are expressed with respect to the total weight of the composition, provided that the sum of the amounts of the components is equal to or less than 100%.

Another aspect of the invention relates to an injection device comprising the topical composition as previously defined.

Another aspect of the invention relates to a kit comprising a delivery device and an injection device comprising the topical composition as previously defined, wherein the delivery device is suitable to be coupled to the injection device.

As mentioned above, the composition of the invention is useful for wound healing, and/or for preventing complications derived from such lesions.

Therefore, another aspect of the invention relates to a topical composition as defined above for use in the treatment of mucosal lesions and/or for the prevention of complications derived from mucosal lesions. This aspect relates to the use of hyaluronic acid or a pharmaceutically or veterinary acceptable salt thereof and a non-absorbable antibiotic for the manufacture of a topical composition as defined above for topical use in the treatment of mucosal lesions and/or for the prevention of complications derived from mucosal lesions. It may also be formulated as a method for the treatment of mucosal lesions and/or for the prevention of complications derived from mucosal lesions in a patient in need thereof, comprising topically applying a therapeutically effective amount of the previously defined topical composition to a subject in need thereof, including a human.

Additionally, the composition of the invention is also useful as sealant treatment in surgical anastomoses in the gastrointestinal tract, such us intestinal anastomoses, which is a surgical procedure to establish communication and restore intestinal continuity between two formerly distant portions of the intestine, after removal of a pathological condition affecting the bowel. It is also useful as sealant treatment in leaks or fistulas in the gastrointestinal tract.

Thus, another aspect of the invention relates to a topical composition as defined above for use as sealant treatment in surgical anastomoses and leaks or fistulas in the gastrointestinal tract. This aspect relates to the use of hyaluronic acid or a pharmaceutically or veterinary acceptable salt thereof and a non-absorbable antibiotic for the manufacture of a topical composition as defined above for topical use a sealant treatment in surgical anastomoses and leaks or fistulas in the gastrointestinal tract. It may also be formulated as a method for the sealant treatment in surgical anastomoses and leaks or fistulas in the gastrointestinal tract in a patient in need thereof comprising topically applying a therapeutically effective amount of the previously defined topical composition to a subject in need thereof including a human.

DETAILED DESCRIPTION OF THE INVENTION

The present invention relates to a topical composition. For the purposes of the present invention, the term "topical" refers to the local administration of the composition other than systemic (i.e., parenteral and enteral) administration. More particularly, it refers to the application of the composition to body surfaces such as the mucosal membranes, such as oral, gastrointestinal and vaginal mucosa.

Unless otherwise stated, all percentages mentioned herein regarding the components of the topical composition are expressed in weight with respect to the total weight of the composition, provided that the sum of the amounts of the components is equal to 100%.

As mentioned above, the topical composition of the invention shows suitable viscosity and adhesion properties. In particular, when the composition contacts the mucosa at body temperature, it has the consistency of a gel, and has the ability to remain adhered to the affected area.

As used herein, "viscosity" refers to a measure of the resistance of a fluid to deform under shear stress and describe the fluid's internal resistance to flow and can be measured as a function of the shear rate by using a rheometer.

For example, the rheological test may be carried out in a Haake device RheoStress equipped with a C60/1°Ti sensor and a "gap set" 0.053 mm, a rotation ramp from 0 to 300 s-1 for 30 seconds. For each trial the evolution of viscosity (η) of the sample according to the speed shear (γ) to 20 and 40 can be measured.

The term "adhesion" as used herein refers to the ability of the topical compositions of the invention to bind to the site of topical application or administration, e.g. mucoses, upon contact, by both chemical and physical means, whereby when they are brought into contact work must be done in order to separate them. The adhesion can be measured by a texture analyser TA.XT Plus. For example, a 40-mm (diameter) disk can be compressed into the gel and redrawn. The method settings, including speed rate at 1 mm/s and distance (depth of the insertion) of 9-mm can be assessed at the desired temperature, e.g. at 22° C. or at 37° C. The adhesion is measured in mN/s units. The more negative the value in mN/s, the more adhesive the topical composition will be. Thus, for example a composition showing a measurement value of −100 mN/s is more adhesive than a composition showing a lower measurement value of −100 mN/s, such as −99 mN/s.

In one particular embodiment, optionally in combination with one or more features of the various embodiments described above or below, the adhesion of the topical composition at body temperature is equal to or lower than −10 mN/s, more particularly from −10 to −4000 mN/s, more particularly from −40 to −4000 mN/s (as measured by the method described above).

In a more particular embodiment, the adhesion of the topical composition at body temperature is equal to or lower than −10 mN/s, more particularly from −10 to −4000 mN/s, more particularly from −40 to −4000 mN/s, when the topical composition comprises one or more adhesive agents able to provide an adhesion such that the adhesion of the topical composition at body temperature is the one defined above.

In a more particular embodiment, the adhesion of the topical composition at body temperature is equal to or lower than −10 mN/s, more particularly from −10 to −4000 mN/s, more particularly from −40 to −4000 mN/s, when the topical composition comprises one or more adhesive agents selected from the group consisting of polyvinyl acetate (PVA), cellulose derivatives (such as cellulose sodium glycolate, methyl cellulose, carboxy methylhydroxyethyl cellulose, hydroxyethyl cellulose, and propyl cellulose), sodium alginate, starch, dextrin, a polyvinyl alcohol, a (poly)vinyl resin, sodium silicate, and pluronic compounds; even more particularly when the topical composition comprises i) a first adhesive agent, more particularly a cellulose ether, more particularly methyl cellulose, particularly in an amount from 0.75 to 3 by weight (wt %) by weight, more particularly from 1 to 2% by weight; and ii) optionally a second adhesive agent, more particularly a pluronic compound, particularly in an amount from 10 to 25 by weight (wt %), more particularly 15 to 20% by weight (wt %).

When the composition shows these adhesion values equal to or lower than −10 mN/s, more particularly from −10 to −4000 mN/s, more particularly from −40 to −4000 mN/s, at body temperature, it has the advantage that it remains adhered to mucosa for a longer period of time.

In another embodiment, optionally in combination with one or more features of the various embodiments described above or below, the viscosity of the topical composition at body temperature is from 0.5 to 1600 Pa·s, more particularly from 1 to 1550 Pa·s (as measured by the method described above).

In a more particular embodiment, the viscosity of the topical composition at body temperature is from 0.5 to 1600 Pa·s, more particularly from 1 to 1550 Pa·s when the topical composition comprises one or more adhesive agents selected from the group consisting of polyvinyl acetate (PVA), cellulose derivatives (such as cellulose sodium glycolate, methyl cellulose, carboxy methylhydroxyethyl cellulose, hydroxyethyl cellulose, and propyl cellulose), sodium alginate, starch, dextrin, a polyvinyl alcohol, a (poly)vinyl resin, sodium silicate, and pluronic compounds; more particularly when the topical composition comprises i) a first adhesive agent, more particularly a cellulose ether, more particularly methyl cellulose, particularly in an amount from 0.75 to 3 by weight (wt %) by weight, more particularly from 1 to 2% by weight; and ii) optionally a second adhesive agent, more particularly a pluronic compound, particularly in an amount from 10 to 25 by weight (wt %), more particularly 15 to 20% by weight (wt %).

When the composition shows these viscosity values from 0.5 to 1600 Pa·s, more particularly from 1 to 1550 Pa·s at body temperature, it forms a particularly thick film, more particularly a film with a thickness from 0.5 to 5 mm, as opposed to a thin film, when applied to the mucosa. This has the advantage that it further improves the physiological healing process of the mucosal lesion.

In another embodiment, optionally in combination with one or more features of the various embodiments described above or below, the adhesion of the topical composition at body temperature is equal to or lower than −10 mN/s, more particularly from −10 to −4000 mN/s, more particularly from −40 to −4000 mN/s; and the viscosity of the topical composition at body temperature is from 0.5 to 1600 Pa·s, more particularly from 1 to 1550 Pa·s.

The topical composition of the invention may also exhibit reverse thermogellation, i.e., it undergoes a change in viscosity when the temperature varies. Thus, for example, the composition may be liquid at room temperature and may form a gel at body temperature.

The liquid state at room temperature facilitates the administration of the composition when it is to be administered e.g. to the gastrointestinal mucosal, by using an appropriate injection device, such as for example a syringe or a jet injector, coupled to a delivery device or system, such as a catheter, which can be introduced via an endoscope. When the composition comes into contact with the mucosa at body temperature, its viscosity increases to a higher viscosity state, hence acquiring the consistency of a gel. This has the advantage that the composition remains on the surface of the affected area facilitating the physiological healing.

Thus, in one particular embodiment, in combination with one or more features of the various embodiments described above or below, the viscosity of the topical composition at body temperature is higher than at room temperature, more particularly the viscosity of the topical composition at body temperature is from 0.5 to 1600 Pa·s, more particularly from 1 to 1550 Pa·s, higher than the viscosity of the topical composition at room temperature.

In another embodiment, optionally in combination with one or more features of the various embodiments described above or below, the adhesion of the topical composition at body temperature is higher than at room temperature. This means that, in this embodiment, the adhesion value in mN/s of the topical composition at body temperature is more negative than the adhesion value in mN/s of the topical composition at room temperature. More particularly the adhesion of the topical composition at body temperature is from 10 to 4000 mN/s (in absolute value), more particularly from 40 to 4000 mN/s (in absolute value), higher than the adhesion of the topical composition at room temperature.

For the purposes of the invention, room temperature refers to a temperature in the range from 20 to 25° C., and body temperature refers to a temperature in the range from 35 to 42° C.

In another embodiment, optionally in combination with one or more features of the various embodiments described above or below, the topical composition of the invention is an aqueous composition, which may be buffered.

As mentioned above, the topical composition of the invention comprises a hyaluronic acid or a pharmaceutically or veterinary acceptable salt thereof. Hyaluronic acid (HA) is a naturally occurring anionic non-sulfated glycosaminoglycan distributed widely throughout connective, epithelial, and neural tissues and part of the extracellular matrix. It consists of multiple repeating disaccharide units of N-acetyl-D-glucosamine and D-glucuronic acid. HA plays an important role in tissue repair by its proliferative and immunomodulatory effect inducing tissue repair promoting healing re-epitelisation instead of scaring.

There is no limitation on the type of the hyaluronic acid salt that can be used, provided that they are pharmaceutically or veterinary acceptable when used for therapeutic purposes. The term "pharmaceutically or veterinary acceptable salt", embraces salts commonly used such as e.g. alkali metal salts. The preparation of hyaluronic acid pharmaceutically acceptable salts can be carried out by methods known in the art. Hyaluronic acid and its salts may differ in some physical properties but they are equivalent for the purposes of the present invention.

Non-limiting examples of pharmaceutically or veterinary acceptable salts include inorganic salts such as sodium hyaluronate, magnesium hyaluronate, potassium hyaluronate, zinc hyaluronate, cobalt hyaluronate, and the like, as well as organic salts such as tetrabutylammonium hyaluronate, and the like. In one particular embodiment, optionally in combination with one or more features of the various embodiments described above or below, the topical composition comprises a hyaluronic acid pharmaceutically or veterinary acceptable salt. More particularly, the pharmaceutically acceptable salt is the sodium salt.

In one particular embodiment, optionally in combination with one or more features of the various embodiments described above or below, the topical composition comprises a hyaluronic acid pharmaceutically or veterinary acceptable salt in an amount from 0.8 to 1.2% by weight (wt %) with respect to the total weight of the topical composition.

In another particular embodiment, optionally in combination with one or more features of the various embodiments described above or below, the hyaluronic acid or a pharmaceutically acceptable salt thereof has a weight average molecular weight (Mw) from $1.5 \times 10^6$ to $4 \times 10^6$ Daltons, more particularly from $1.7 \times 10^6$ to $2 \times 10^6$ Daltons.

The topical composition also comprises one or more adhesive agents which contribute to the adhesion of the composition. Non limiting examples of adhesive agents include polyvinyl acetate (PVA), cellulose derivatives such as cellulose sodium glycolate, methyl cellulose, carboxy methylhydroxyethyl cellulose, hydroxyethyl cellulose, and propyl cellulose, sodium alginate, starch, dextrin, a polyvinyl alcohol, a (poly)vinyl resin, sodium silicate, pluronic compounds, and the like. When the adhesive agent is sodium alginate, a compound containing divalent ions, such as $CaCl_2$), is preferably present in the topical composition.

Pluronic compounds, also named as poloxamers, are block copolymers of propylene oxide and ethylene oxide. In one embodiment of the invention, the polyoxypropylene content in the poloxamer is from 30 to 90 wt %, more particularly about 70%. In one embodiment of the invention, the polyoxypropylene molecular mass in the poloxamer is from 1000 to 5000 g/mol, more particularly about 4000. An example of a poloxamer is oloxamer 407 (Pluronic® F-127.

In one particular embodiment, optionally in combination with one or more features of the various embodiments described above or below, the topical composition comprises one or more adhesive agents in an amount from 1 to 20% by weight (wt %) with respect to the total weight of the topical composition.

In one particular embodiment, optionally in combination with one or more features of the various embodiments described above or below, the adhesive agent is a cellulose ether. More particularly, the adhesive agent is methyl cellulose. More particularly, the adhesive agents is methyl cellulose having a percentage of methoxy substitution from 25 to 33% and a weight average molecular weight from 10000 to 20000 Daltons. More particularly, the cellulose ether is comprised in the topical composition of the invention in amount from 0.75 to 3% by weight (wt %), more particularly from 1 to 2% by weight (wt %), with respect to the total weight of the topical composition.

In another particular embodiment, optionally in combination with one or more features of the various embodiments described above or below, the adhesive agent is a pluronic compound. More particularly, the pluronic compound is comprised in the topical composition of the invention in amount from 10 to 25% by weight (wt %), more particularly from 15 to 20% by weight (wt %), with respect to the total weight of the topical composition.

In another particular embodiment, optionally in combination with one or more features of the various embodiments described above or below, the topical composition comprises two adhesive agents: a) a first adhesive agent, more particularly a cellulose ether, more particularly methyl cellulose, in an amount from 0.75 to 3 by weight (wt %) by weight, more particularly from 1 to 2% by weight, with respect to the total weight of the topical composition; and b) a second adhesive agent, more particularly a pluronic compound, in an amount from 10 to 25 by weight (wt %), more particularly 15 to 20% by weight (wt %), with respect to the total weight of the topical composition.

The topical composition comprises a non-absorbable antibiotic. The term "non-absorbable antibiotic" refers to a compound having antibacterial properties which is poorly or not absorbed from the lumen, i.e., the non-absorbable antibiotic provides activity only locally in the gut and has a negligible systemic absorption. Non-absorbable antibiotics, unlike systemically available antibiotics, maintain a topical action without systemic and side effects and the lack of resistant bacterial strains may allow prolonged and repeated treatments.

In one particular embodiment, optionally in combination with one or more features of the various embodiments described above or below, the non-absorbable antibiotic is selected from the group consisting of gentamicin, vancomycin, nystatin, neomycin, colistin, kanamycin, polimixin, and rifaximin. More particularly, the non-absorbable antibiotic is rifaximin.

In another particular embodiment, optionally in combination with one or more features of the various embodiments described above or below, the topical composition comprises a non-absorbable antibiotic in an amount from 1.8 to 2.2% by weight with respect to the total weight of the topical composition.

The topical composition of the invention may also comprise further components, such as for example mineral cofactors, more particularly cofactors for Matrix metalloproteinases (MMPs). As used herein, "cofactor" refers to an agent that activates an enzyme, more particularly an endopeptidase, such as MMP.

Examples of mineral cofactors of the formulation may include zinc compounds, calcium compounds, manganese compounds, and magnesium compounds. Particularly suitable mineral cofactors are zinc cofactors such as zinc oxide, zinc gluconate, zinc amino acid chelates or mixtures thereof.

In one particular embodiment, optionally in combination with one or more features of the various embodiments described above or below, the topical composition comprises a mineral cofactor, more particularly a mineral cofactors for Matrix metalloproteinases (MMPs), more particularly a zinc cofactor, even more particularly zinc oxide. The cofactor may be present in the composition in an amount from 4 to 10 wt % by weight, more particularly 6 to 8% by weight, with respect to the total weight of the topical composition.

In one particular embodiment, optionally in combination with one or more features of the various embodiments described above or below, the invention refers to a topical composition, particularly an aqueous topical composition, which comprises:
  a) a hyaluronic acid or a pharmaceutically or veterinary acceptable salt thereof, particularly a hyaluronic acid salt in an amount from 0.6 to 1.5% by weight (wt %), more particularly from 0.8 to 1.2% by weight (wt %);
  b) one or more adhesive agents, particularly i) a first adhesive agent, more particularly a cellulose ether, more particularly methyl cellulose, particularly in an amount from 0.75 to 3 by weight (wt %) by weight, more particularly from 1 to 2% by weight; and ii) optionally a second adhesive agent, more particularly a pluronic compound, particularly in an amount from 10 to 25 by weight (wt %), more particularly 15 to 20% by weight (wt %);
  c) a non-absorbable antibiotic, particularly rifaximin, in an amount from 1.5 to 2.5 wt % by weight, more particularly 1.8 to 2.2% by weight; and
  d) optionally a cofactor, particularly zinc oxide, particularly in an amount from 4 to 10 wt % by weight, more particularly 6 to 8% by weight; wherein all percentages are expressed with respect to the total weight of the composition, provided that the sum of the amounts of the components is equal to or less than 100%.

In another particular embodiment, optionally in combination with one or more features of the various embodiments described above or below, the invention refers to a topical composition, particularly an aqueous topical composition, which consists of:
  a) a hyaluronic acid or a pharmaceutically or veterinary acceptable salt thereof, particularly a hyaluronic acid salt, in an amount from 0.6 to 1.5% by weight (wt %), more particularly from 0.8 to 1.2% by weight (wt %);
  b) one or more adhesive agents, particularly i) a first adhesive agent, more particularly a cellulose ether, more particularly methyl cellulose, particularly in an amount from 0.75 to 3 by weight (wt %) by weight, more particularly from 1 to 2% by weight; and ii) optionally a second adhesive agent, more particularly a pluronic compound, particularly in an amount from 10 to 25 by weight (wt %), more particularly 15 to 20% by weight (wt %);
  c) a non-absorbable antibiotic, particularly rifaximin, in an amount from 1.5 to 2.5 wt % by weight, more particularly 1.8 to 2.2% by weight;
  d) optionally a cofactor, particularly zinc oxide, particularly in an amount from 4 to 10 wt % by weight, more particularly 6 to 8% by weight; and
  e) water or a buffer, particularly in an amount from 58 to 83.15 wt % by weight, more particularly 66.6 to 75.4% by weight;
wherein all percentages are expressed with respect to the total weight of the composition, provided that the sum of the amounts of the components is equal to 100%.

The topical composition of the invention is biodegradable. This means that it is bioresorbed or degraded or broken down into components that are well tolerated by the body of the patient. Thus, there is no need to remove the composition of the invention once applied to the body.

The composition of the invention may be prepared by mixing their components, particularly in water or a buffer, and stirring until achieving the complete dissolution of the components.

The composition of the invention is to be administered in a therapeutically effective amount sufficient to cover the affected mucosal area.

A mentioned above it also forms part of the injection device comprising the topical composition as previously defined, and a kit comprising this injection device and a delivery device that is suitable to be coupled to the injection device.

The injection device may be any device appropriate for comprising the composition of the invention that is suitable to be coupled or connected to the delivery device. Non-limiting examples of injection devices include syringes or jet injectors.

The delivery device can be any tubular device having a lumen that is suitable to be coupled or connected to the injection device and is capable to deliver the composition of the invention to its action site. Non-limiting examples of delivery devices include catheters.

In one embodiment, optionally in combination with one or more features of the various embodiments described above or below, the delivery device has a smaller diameter than the working channel diameter of the endoscope.

For example, when the topical composition is to be administered to the gastrointestinal mucosal after therapeutic endoscopy, it can be applied by using an appropriate delivery device or system such as a catheter which can be introduced via an endoscope. Thus, for this therapeutic application, the delivery device has a smaller diameter than the working channel diameter of the endoscope.

The endoscope can be the same endoscope used to carry out the therapeutic endoscopy.

Generally, gastrointestinal endoscopes have working channel diameter in the range of 2.8-3.4 mm and a length of 160 cm. In one particular embodiment, the delivery device has a diameter lower than 2.8 mm, more particularly, lower than 2.2 mm, and a length higher than 160 cm, more particularly higher than 200 cm. For example, the length of the delivery device may be 230 cm.

The skilled in the art will know the injection device to be chosen depending on the delivery device to be used so that the composition may be administered by using an adequate force.

For example, in one embodiment, optionally in combination with one or more features of the various embodiments described above or below, the invention relates to a delivery device, particularly a catheter, comprising the topical composition as previously defined, wherein the delivery device has a diameter in the range of 2.0-2.2 mm, and the injector device is a syringe. In this case, the composition may be administered by applying a force of about 2-3 atmospheres.

In another embodiment, optionally in combination with one or more features of the various embodiments described above or below, the invention relates to a delivery device, particularly a catheter, comprising the topical composition as previously defined, wherein the delivery device has a diameter in the range of 0.6-0.8 mm, and the injector device is a jet injector. In this case, the composition may be administered by applying a force of about more than 5 atmospheres.

The expression "therapeutically effective amount" as used herein, refers to the amount of the composition of the invention that, when administered, is sufficient to prevent development of, or alleviate to some extent, one or more of the symptoms of the disease which is addressed. The specific dose of the topical composition to obtain a therapeutic benefit may vary depending on the particular circumstances of the case. A typical amount to be sprayed is 0.5 to 2 mL per $cm^2$ of mucosal lesion.

For the purposes of the invention, each component of the topical composition as defined above must be pharmaceutically or veterinary acceptable in the sense of being compatible with the other ingredients of the composition. It must also be suitable for use in contact with the tissue or organ of humans and animals without excessive toxicity, irritation, allergic response, immunogenicity or other problems or complications commensurate with a reasonable benefit/risk ratio.

As mentioned above, the topical composition as defined above may be used in the treatment of mucosal lesions and/or for the prevention of complications derived from mucosal lesions.

The composition of the invention is suitable for being administered to a mucosa, and/or suitable for healing mucosal lesions, in particular, mucosal lesions induced by thermal injury, and more particularly, thermal injury associated or caused by therapeutic endoscopy.

In one particular embodiment, optionally in combination with one or more features of the various embodiments described above or below, the invention relates to the topical composition as defined above for use in the treatment and/or prevention of mucosal lesions induced by thermal injury, more particularly, thermal injury associated or caused by therapeutic endoscopy.

As used herein, thermal injury refers to an injury caused by either extreme cold or heat which alters or damages the tissue, chemical or electrical burn which alters or damages the tissue, or chemical or electrical trauma which alters or damages the tissue.

Generally, the therapeutic endoscopy includes polypectomy, Endoscopic Mucosal Resection (EMR), and Endoscopic Submucosal Disection (ESD).

In another particular embodiment, optionally in combination with one or more features of the various embodiments described above or below, the invention relates to a topical composition as defined above for use in the prevention of postpolypectomy syndrome.

In another particular embodiment, optionally in combination with one or more features of the various embodiments described above or below, the invention relates to a topical composition as defined above for use in the treatment and/or prevention of mucosal lesions selected from the group consisting of gastrointestinal tract mucosal lesions, vaginal mucosal lesions and oral lesions.

In another particular embodiment, optionally in combination with one or more features of the various embodiments described above or below, the invention relates to the topical composition as defined above for use in the treatment and/or prevention of mucosal lesions secondary to radiotherapy (actinic proctitis).

In another particular embodiment, optionally in combination with one or more features of the various embodiments described above or below, the invention relates to the topical composition as defined above for use in the treatment and/or prevention of mucosal lesions which are mucosal perforations, more particularly gastrointestinal perforations. More particularly, the invention relates to the topical composition as defined above may be used as adjuvant therapy to mechanical treatments in gastrointestinal perforations, more particularly, gastrointestinal perforations secondary to endoscopy.

As mentioned above, the topical composition as defined above may also be used as sealant treatment in surgical anastomoses and leaks or fistulas in the gastrointestinal tract, in particular to prevent leaks after surgery.

As mentioned above, the compositions of the invention show a higher mucosal healing rate and a higher physiological healing, while reducing at the same time the fibrotic healing in comparison to a composition consisting only of hyaluronic acid.

As used herein, the term "physiological healing" refers to the restoration of damaged living tissue, organs and biological system to normal function. It is the process by which the cells in the body regenerate and repair to reduce the size of a damaged or necrotic area. The term "fibrotic healing" refers to the temporal and progressive deposition of fibrous tissue over the affected tissue during fibrosis. Generally, when fibrotic healing occurs, a scar is formed which may be cumbersome and vulnerable to repeated trauma.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Chemicals Used:
Hyaluronic Acid Sodium Salt (from Rooster Comb):
Also known as: Poly(beta-glucuronic acid-[1→3]-beta-N-acetylglucosamine-[1→4]); Average Molecular weight: $1.5 \times 10^6 - 4 \times 10^6$ Daltons.
Methyl Cellulose:
Also known as: Methocel A®, Methylcellulose A, Methyl cellulose ether. Approximate Molecular Weight: 14000 g/mol: Cellulose, with methoxy substitution between 27.5-31.5% (w).
Rifaximin:
Also known as: Rifacol, 4-Deoxy-4'-methylpyrido[1',2'-1,2]imidazo[5,4-c]rifamycin SV; Molecular Formula: $C_{43}H_{51}N_3O_{11}$; Molecular Weight: 785.88 g/mol.
Pluronic® F127:
Also known as: poloxamer 407, PPG-PEG-PPG; Pluronic®-F-68; Poly(ethylene glycol-ran-propylene glycol); Polyoxyethylene-polyoxypropylene Block Copolymer; Molecular Formula: $C_5H_{14}O_4$; Molecular Weight: 138.16226 g/mol. Average molecular weight: 12600 Daltons.

Example 1

Pluronic F127 (6 g) was added to distilled water (30 mL) in a 100 mL glass and was stirred at 500 rpm until its complete dissolution. Then, hyaluronic acid sodium salt (0.3 g) was added and stirred at 500 rpm until its complete dissolution. Then, methyl cellulose (0.6 g) was added and stirred again to 500 rpm until its complete dissolution. Finally, rifaximin (0.3 g) was added and stirred at 500 rpm for 30 minutes. Thus, the following composition was obtained:

| Component | Amount (% w/w) |
| --- | --- |
| Hyaluronic acid sodium salt | 1 |
| Methylcellulose | 2 |
| Pluronic acid F127 | 20 |
| Rifaximin | 2 |
| Water | 75 |
| Total | 100 |

Example 2

Hyaluronic acid sodium salt (0.1 g) was added to distilled water (10 mL) in a 100 mL glass and was stirred at 500 rpm until its complete dissolution. Then, methyl cellulose (0.2 g) was added and stirred again to 500 rpm until its complete dissolution. Finally, rifaximin (0.2 g) was added and stirred at 500 rpm for 30 minutes. Thus, the following composition was obtained:

| Component | Amount (% w/w) |
| --- | --- |
| Hyaluronic acid sodium salt | 1 |
| Methylcellulose | 2 |
| Rifaximin | 2 |
| Water | 95 |
| Total | 100 |

Hydrogel Characterization
Texture Analysis
A Texture Analyser TA.XT Plus was used to determine the texture properties of the hydrogels. A 40 mm (diameter) disk was compressed into the gel and redrawn. The method settings, including speed rate at 1 mm/s and distance (depth of the insertion) of 9 mm were assessed at 22° C. and 37° C. Hydrogels of Examples 1-2 were tested and the results shown in table 1 below were obtained:

TABLE 1

| | At 22° C. | | At 37° C. | |
| --- | --- | --- | --- | --- |
| | Adhesion (mN/s) | SD | Adhesion (mN/s) | SD |
| Example 1 | −24.48 | 5.34 | −3992.93 | 536.21 |
| Example 2 | −21.68 | 4.24 | −41.25 | 5.47 |

For the hydrogels of the invention it was observed that a temperature increase resulted in a significant higher adhesion of the product.

Figure 1:
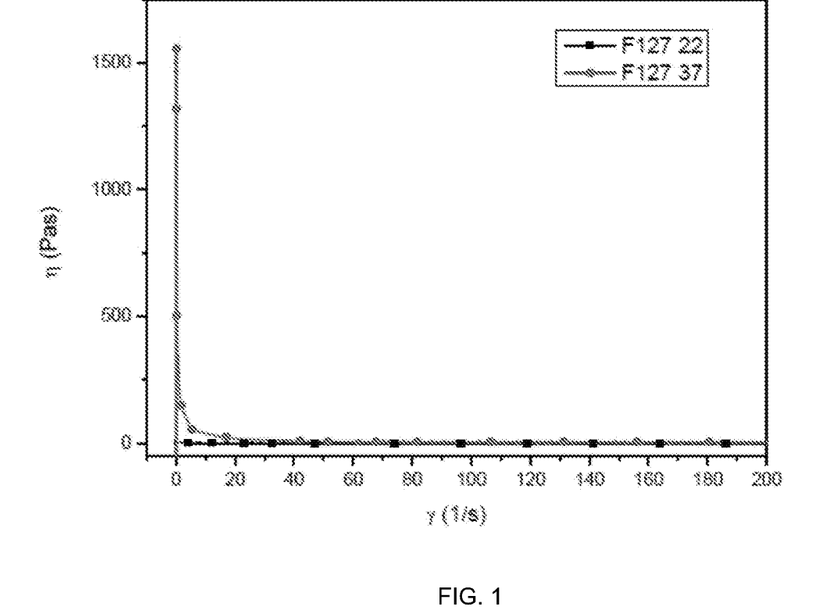
FIG. 1 shows the evolution of the viscosity of the hydrogel of Example 1 of the invention according to the speed of shear.

Rheological Assay
A rheological study was performed in a rheometer Haake RheoStress with a C60/1° Ti probe and a gap set of 0.053 mm. Viscosity (i) was measured as a function of shear rate (γ) of 0 to 300 $s^{-1}$ at 22° C. and 37° C. Hydrogels of Examples 1-2 were tested and the obtained results are shown in FIGS. 1 and 2 respectively.

According to the results obtained, the hydrogel of Example 1 presented a non-Newtonian fluid behaviour. A non-Newtonian fluid is a fluid whose viscosity is not defined or constant, varying with temperature and the shear stress applied to it. The hydrogel of Example 1 conformed well to the model Herschel-Bulkley rheological ($\eta=\tau 0/\gamma+K\cdot\gamma n-1$) where $\eta$ is the apparent viscosity and $\gamma$ the shear rate. FIG. 1 shows the evolution of the represented viscosity of the hydrogel of Example 1 according to the speed of shear. The product showed an increase in viscosity with temperature, since the initial viscosity (22° C.) increased from <1 Pa·sec. to 1550 Pa·sec. at 37°.

Figure 2:
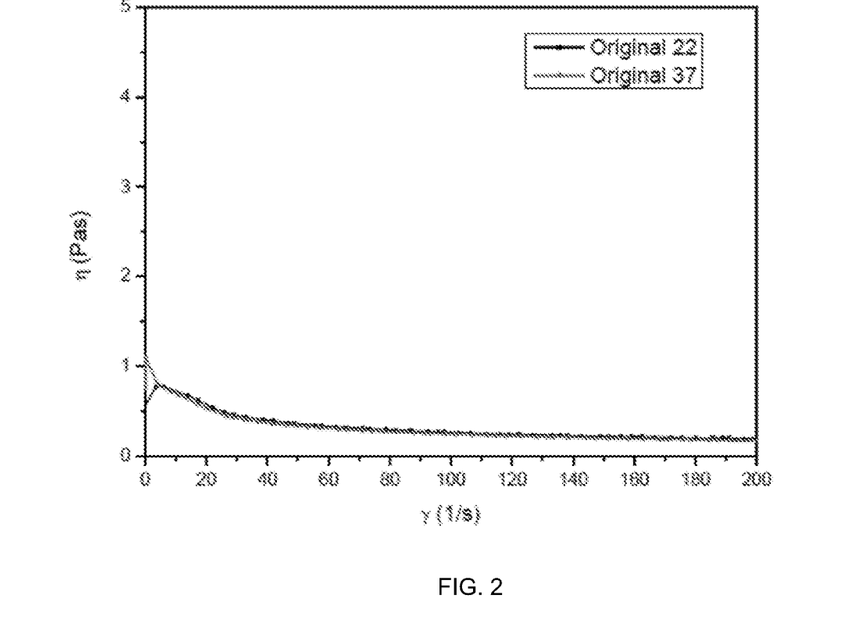
FIG. 2 shows the evolution of the viscosity of the hydrogel of Example 2 of the invention according to the speed of shear.

FIG. 2 shows the evolution of the represented viscosity of the hydrogel of Example 2 according to the speed of shear.

Preclinical Studies in Rats and Pigs

Study 1: Endoscopic Study in Rats

Thirty-two male Sprague-Dawley rats (400-450 g) were used in this study. Rats were acclimatized for a minimum of 7 d preoperatively. Rats were kept at constant room temperature (20-22° C.) with a relative humidity (27-31%) with aeration under an alternating 12-h cycle of fluorescent light and darkness. The rats were housed individually in polycarbonate box cages with free access to water and food (Teklad Global 2014; Harlan Laboratories Models SL, Barcelona, Spain). Rats suffered minimal pain and distress because of the use of anesthesia. The protocol was approved by the Institutional Animal Care and Use Committee of Hospital Universitari Germans Trias i Pujol.

The animals had free access to water, but food was withdrawn 8 h before the initiation of bowel preparation. A rectal enema with saline solution was performed immediately before colonoscopy. Colonoscopy was performed with a gastroscope Olympus Lucera 260-HDTV/NBI/AFI. Hot biopsy forceps (Olympus Medical System, Tokio, Japan) were used for all treatments. The electrosurgical generator used was the Olympus PSD-2 (Olympus Medical System). Mucosa lesion to reproduce microperforation of the colon was obtained following the model described in Lorenzo-Zuniga V, Microperforation of the colon: animal model in rats to reproduce mucosal thermal damage. J. Surg. Res. 2014, 188(2):415-8.

After a 24-h fasting period with free access to drinking water, rats were anesthetized by isoflurane inhalation (1.5% with 98% $O_2$) and placed in a supine position. Remaining faeces were flushed away by injecting water through the anus. A drop of lubricating jelly (Aquagel; Ecolab, Leeds, England) was applied on the anal sphincter to facilitate insertion of the endoscope. The endoscope was then gently passed through the anus and further introduced under endoscopic vision. Water was injected through the endoscope's working channel to visualize the lumen of the colon. Occasionally, the colon was inflated with air for better visualization of the lumen. The monopolar coagulation device was then passed through the accessory channel of the endoscope, and a uniform and consistent pulling force was applied to grasp the colonic mucosa in the proximal left colon, at 6 cm from anal margin, for the creation of the electrocautery lesion.

Animals were randomized to receive (through the endoscopic working channel) 2-mL of one of the following treatments (8-rats each): saline (control), sodium hyaluronic acid sodium salt 1% w/w and (comparative example) and the hydrogel of the Example 1-2. The treatment was applied as a shield over the lesion (endoscopic shielding technique).

Rats were endoscopically followed at 48 h. TNF-α plasma levels were determined at 48 h using a colorimetric assay kit (TNF-α rat ELISA kit, Abcam®). Rats were sacrificed after 7 days by anesthetic overdose (60-mg pentobarbital intraperitoneally). After sacrifice, the colon was collected and rinsed with ice-cold Krebs solution. The colon was opened longitudinally and pinned out on a Petri dish to examine colonic mucosa. The mucosal surface of the distal colon was inspected with a binocular microscope (Harvard Apparatus; Panlab, Barcelona, Spain).

Full-thickness samples of 4 cm were taken from proximal left colon. Segments were fixed in 4% formaldehyde for 24 h, embedded in paraffin, and cross sections of 5 mm were stained with hematoxylin and eosin. Histologic sections were examined using a conventional microscope (Olympus). Histological study of the specimens allowed to assess diameter of lesions (previous at 48 h assessed under endoscopic view), mucosal healing rate and fibrotic or physiological healing. During the follow-up mortality (exitus) and perforation rate was reported. The following results were obtained:

TABLE 2

| In vivo results | 9 g/L Sodium chloride (control) | Hyaluronic acid sodium salt (1%) | Example 1 | Example 2 |
|---|---|---|---|---|
| N | 8 | 8 | 8 | 8 |
| Exitus n (%) | 4/8 (50) | 2/8 (25) | 0/8 (0) | 0/8 (0) |
| Perforation at 7 days n (%) | 4/4 (100) | 2/6 (33.3) | 0/8 (0) | 2/8 (25) |
| Diameter of lesions at 48 h (cm$^2$)* | 0.56 (0.55-0.59) | 0.55 (0.51-0.58) | 0.57 (0.54-0.60) | 0.57 (0.53-0.59) |
| Diameter of lesions at 7 days (cm$^2$) | 0.39 (0.38-0.42) | 0.29 (0.21-0.32) | 0.17 (0.09-0.25) | 0.19 (0.18-0.20) |
| Mucosal healing rate (%) | 30.3 | 47.2 | 70.3 | 66.6 |
| Fibrotic healing (%) | 4/4 (100) | 2/6 (33.3) | 2/8 (25) | 2/8 (25) |
| Physiological healing (%) | 0/4 (0) | 4/6 (66.6) | 6/8 (75) | 6/8 (75) |
| Basal TNFα (pg/mL) | 255.54 ± 2.47 | — | — | — |
| 48 h TNFα (pg/mL) | 627.58 ± 0.52 | 338.10 ± 17.2 | 289.54 ± 0.64 | 344.46 ± 28.2 |

*Measured under endoscopic view

Results in table 2 showed that the hydrogel of the invention obtained the best results in comparison with saline and hyaluronic acid sodium salt, avoiding mortality, and avoiding or reducing the risk of perforation at 7 days. Mucosal healing rate (percentage of mucosal restoration) at 7 days was significantly higher with the hydrogels of the invention, as can be observed from the evolution of diameter of lesions from 48 h to 7 days. Physiological healing, which is very important to avoid submucosal fibrosis, and defined as the restoration of histological and functional properties of the mucosal layer, was significantly higher with the hydrogel of Example 1 and 2 (6 of 8 animals, 75%) than in saline (0 of 4 animals, 0%) and hyaluronic acid (4 of 6 animals, 66.6%).

Computed Tomography (CT) Study

In vivo X-ray Microtomograph (SkyScan 2002, Aartselaar, Belgium) was used in order to obtain a 3D image of distal colon (scar area) as described in Bartoli R. et al., World J. Gastrointest. Endosc. 2013, 5(5):226-30. Briefly, after therapeutic endoscopy, animals were placed in the scanning area under anesthesia with isofluorane. To visualize the hydrogel, barium contrast was mixtured with the product. Acquisition images for 3D reconstruction of the distal colon lasted over 20 min with a resolution of 32 μm.

CT study showed that hydrogel remained adhered to the scar area for at least 36 hours after endoscopic administration.

Study 2: Endoscopic Study in Pigs

Eight female pigs (35-40 kg) were included in the study. Animals were acclimatised for 7 days prior to endoscopic procedures.

Study Design

Animals underwent endoscopic mucosal resection (EMR) on left colon located at 30 cm from anal margin. Animals were treated with Example 1, applied as a shield over the lesion covering the total surface of the ulcer (endoscopic shielding technique, EST), as follows:
- A)—Submucosal saline injection+EMR 30 cm to anal margin (n=4)
- B)—Submucosal saline injection+EMR+Example 1 (EST treatment 30
- cm to anal margin, n=4)

Colonic EMR-Induced Lesions in Pigs

Endoscopic procedures were performed with Olympus Lucera 260-HDTV/NBI/AFI video gastroscope with an outer diameter of 9.5 mm, working channel 2.8 mm (Olympus, Tokio), under sedation with propofol. A 23-gauge injection needle (MTW, Wesel, Germany) was passed through the endoscopic accessory channel. Mucosal elevations were created at 30-cm to anal margin by submucosal injection with saline. EMR with snare polypectomy and blended current was performed after injection. Animals were randomly allocated to receive Example 1 or saline (n=4 each), and underwent endoscopic follow-up at 7 and 14 days after the creation of mucosal lesions. After this time, pigs were then euthanized using intravenous potassium chloride under sedation and necropsied, to obtain colonic samples as described above. Also, and before the sacrifice, one additional EMR-induced lesion was assessed at 15 cm from anal margin to all animals in order to obtain "basal" lesions.

Assessments

Mucosal healing was evaluated as mean ulcerated area after 7 and 14 days. Measurement of mucosal lesion was performed under endoscopic view during follow-up as comparison with opened forceps (5 mm) or by direct measurement with the specimen.

Thermal injury was evaluated with a 1 to 4 scale: 1) mucosal necrosis; 2) submucosal necrosis; 3) transmural necrosis; 4) peritonitis, microperforation. To perform this, segments were fixed in 4% formaldehyde for 24 h, embedded in paraffin and cross sections of 5 μm were stained with haematoxylin and eosin (H&E). Histological sections were examined using a conventional microscope (Olympus, Shinjuku-ku, Tokyo, Japan).

Results

All animals survived at the end of the study. Basal mean ulcerated area induced by EMR was comparable in both groups (A=2.12±1.45 $cm^2$, B=2.57±1.53 $cm^2$; p=n.s.). Similarly, induced thermal injury was comparable in both groups (A=2.45±0.46 vs A and B=2.75±0.46; p=n.s.). Mucosal healing rate at week 2 (percentage of mucosal restoration) were significantly higher in animals treated with Example 1 (B=90.2±3.9% vs A=73.1±12.6%; p=0.002).

For reasons of completeness, various aspects of the invention are set out in the following numbered clauses:

Clause 1. A topical composition comprising:
a) a hyaluronic acid or a pharmaceutically or veterinary acceptable salt thereof,
b) one or more adhesive agents, and
c) a non-absorbable antibiotic.

Clause 2. The topical composition according to clause 1, having an adhesion of the at body temperature which is equal to or lower than −10 mN/s.

Clause 3. The topical composition according to any of the clauses 1-2, having a viscosity at body temperature which is from 0.5 to 1600 Pa·s.

Clause 4. The topical composition according to any of the clauses 1-3, which is an aqueous composition.

Clause 5. The topical composition according to any of the clauses 1-4, wherein the hyaluronic acid or a pharmaceutically or veterinary acceptable salt is hyaluronic acid sodium salt.

Clause 6. The topical composition according to any of the clauses 1-5, wherein the hyaluronic acid or a pharmaceutically or veterinary acceptable salt thereof is present in the composition in an amount from 0.6 to 1.5 wt % with respect to the total weight of the topical composition.

Clause 7. The topical composition according to any of the clauses 1-6, wherein the adhesive agent is a cellulose ether.

Clause 8. The topical composition according to any of the clauses 1-7, wherein the adhesive agent is present in the composition in an amount from 0.75 to 3 wt % with respect to the total weight of the topical composition.

Clause 9. The topical composition according to any of the clauses 1-8, wherein the non-absorbable antibiotic is rifaximin.

Clause 10. The topical composition according to any of the clauses 1-9, wherein the non-absorbable antibiotic is present in the composition in an amount from 1.5 to 2.5 wt % with respect to the total weight of the topical composition.

Clause 11. The topical composition according to any of the clauses 1-10, which comprises a pluronic compound.

Clause 12. A topical composition as defined in any of the clauses 1-11, for use in the treatment and/or prevention of mucosal lesions or skin ulcers.

Clause 13. The topical composition for use according to clause 12, wherein the mucosal lesions are induced by thermal injury associated/caused by therapeutic endoscopy.

Clause 14. A topical composition as defined in any of the clauses 1-11, for use in the prevention of postpolypectomy syndrome.

Clause 15. A topical composition as defined in any of the clauses 1-11, for use as adjuvant therapy to mechanical treatments in gastrointestinal perforations, or as sealant treatment in surgical anastomoses and leaks or fistulas in gastrointestinal tract.

REFERENCES CITED IN THE APPLICATION

Niimi K. et al., "Subserosal injection of hyaluronic acid may prevent perforation after endoscopic resection", World J. Gastrointest. Endosc. 2009, 1(1):61-4.

Lorenzo-Ztniga V. et al., "Microperforation of the colon: animal model in rats to reproduce mucosal thermal damage", J. Surg. Res. 2014, 188(2):415-8.

Bartoli R. et al., "Colonoscopy in rats: An endoscopic, histological and tomographic study", World J. Gastrointest. Endosc. 2013, 5(5):226-30.

The invention claimed is:

1. A topical composition comprising:
a) from 0.6 to 1.5 wt % of a hyaluronic acid or a pharmaceutically or veterinary acceptable salt thereof,
b) two adhesive agents: a first adhesive agent which is selected from the group consisting of sodium alginate, starch, polyvinyl alcohol, and sodium silicate, and is present in an amount from 0.75 to 3 wt %, and a second adhesive agent which is a pluronic compound and is present in an amount from 10 to 25 wt %, and c) from 1.5 to 2.5 wt % of a non-absorbable antibiotic;

wherein the topical composition exhibits reverse thermogellation and wherein all percentages are expressed with respect to the total weight of the composition, provided that the sum of the amounts of the components is equal to or less than 100%.

2. The topical composition according to claim 1, having an adhesion at body temperature which is equal to or lower than −10 mN/s.

3. The topical composition according to claim 1, having a viscosity at body temperature which is from 0.5 to 1600 Pa·s.

4. The topical composition according to claim 1, which is an aqueous composition.

5. The topical composition according to claim 1, wherein the hyaluronic acid or a pharmaceutically or veterinary acceptable salt is hyaluronic acid sodium salt.

6. An injection device comprising the topical composition as defined in claim 1.

7. A kit comprising the injection device as defined in claim 6, and a delivery device suitable to be coupled to the injection device.

8. A method for the treatment of mucosal lesions and/or for the prevention of complications derived from mucosal lesions comprising topically applying a therapeutically effective amount of a topical composition as defined in claim 1 to a subject in need thereof, including a human.

9. The method according to claim 8, wherein the composition is to be administered by an appropriate delivery device.

10. The method according to claim 8, wherein the mucosal lesions are induced by thermal injury associated/caused by therapeutic endoscopy.

11. A method for the prevention of postpolypectomy syndrome comprising topically applying a therapeutically effective amount of a topical composition as defined in claim 1 to a subject in need thereof, including a human.

12. A method for the sealant treatment in surgical anastomoses and leaks or fistulas in gastrointestinal tract comprising topically applying a therapeutically effective amount of a topical composition as defined in claim 1, to a subject in need thereof, including a human.

13. A method for the adjuvant therapy to mechanical treatments in gastrointestinal perforations comprising topically applying a therapeutically effective amount of a topical composition as defined in claim 1 to a subject in need thereof, including a human.

14. The topical composition according to claim 1, wherein the non-absorbable antibiotic is rifaximin.

* * * * *